United States Patent [19]

Monnier et al.

[11] Patent Number: 4,942,263
[45] Date of Patent: Jul. 17, 1990

[54] PREPARATION OF ALDEHYDES

[75] Inventors: John R. Monnier, Fairport; Peter J. Muehlbauer, Spencerport, both of N.Y.

[73] Assignee: Eastman Kodak Company, Rochester, N.Y.

[21] Appl. No.: 337,233

[22] Filed: Apr. 13, 1989

[51] Int. Cl.$^5$ .............................................. C07C 45/34
[52] U.S. Cl. .................................... 568/476; 568/470; 568/475
[58] Field of Search ................. 568/475, 476, 478, 470

[56] References Cited

U.S. PATENT DOCUMENTS

| | | | |
|---|---|---|---|
| 3,840,602 | 10/1974 | McCain et al. | 568/478 |
| 3,923,881 | 12/1975 | Murib et al. | 568/478 |
| 4,415,757 | 11/1983 | Pyke et al. | 568/475 |
| 4,477,997 | 10/1984 | Rao | 568/473 |

OTHER PUBLICATIONS

Greenen et al., Journal of Catalysis vol. 77, (1982), pp. 499–509.

*Primary Examiner*—Werren B. Lone
*Attorney, Agent, or Firm*—Robert A. Linn

[57] ABSTRACT

Olefins which are free of allylic hydrogens, and which contain two hydrogens bonded to a carbon atom which is bonded to another carbon by a double bond, from aldehydes when reacted with oxygen in the presence of an acidic silver catalyst, such as silver dispersed on $\gamma$-alumina. For example, 1,3-butadiene is oxidized to crotonaldehyde.

10 Claims, No Drawings

PREPARATION OF ALDEHYDES

FIELD OF THE INVENTION

This invention relates to the partial oxidation of non-allylic olefins to produce an aldehyde. In this process, molecular oxygen is used as the oxidant, and a catalyst is employed. The catalyst may comprise silver on an acidic support, e.g., an acidic alumina having a moderate or higher acidity. In a preferred embodiment, the invention relates to preparation of crotonaldehyde from 1,3-butadiene.

BACKGROUND OF THE INVENTION

Various methods are known for production of aldehydes. These methods include the oxidation of primary alcohols, the condensation of aldehydes, and the addition of carbon monoxide to a suitable olefin. Aldehydes are valuable chemical intermediates. In view of the general utility of aldehydes, new methods for making them are of high interest.

RELATED ART

U.S. Pat. No. 2,709,173 pertains to silver catalyzed epoxidation and suggests that lower molecular weight hydrocarbon olefins are adaptable to the preparation of olefin oxides. It states that those which are normally gaseous, such as ethylene, propylene, butene-1, butene-2, and butadiene are more suitable, with ethylene being preferred.

U.S. Pat. No. 3,465,043 discloses isomerization of butadiene monoepoxide to crotonaldehyde (2-butenal), in the presence of a rhodium containing catalyst.

U.S. Pat. No. 3,840,602 pertains to the preparation of unsaturated aldehydes by the oxidation of olefins of at least 3 carbon atoms. The disclosed method uses a silver catalyst modified with a Group VIII metal compound, preferably selected from the trichlorides and tribromides of rhodium and iridium. Butadiene is not mentioned as an applicable olefin.

U.S. Pat. Nos. 4,429,055 and 4,474,997 disclose catalysts comprising a boron phosphate impregnated with silver. The catalyst is used to oxidize olefins such as propylene, butene-1 and butadiene-1,3. The reported products from oxidation of butadiene are furan, dihydrofuran, and trihydrofuran; crotonaldehyde is not mentioned.

SUMMARY OF THE INVENTION

This invention pertains to the partial oxidation of olefins which (1) have two hydrogens bonded to a carbon atom which is bonded to another carbon atom by a double bond, and (2) which do not have an allylic hydrogen. In this invention, such olefins are oxidized to an aldehyde. As will be recognized by a skilled practitioner, the aldehyde is not formed by an oxidative dehydrogenation.

The process of this invention employs molecular oxygen as the oxidant. The catalyst employed is elemental silver, preferably on an acidic support. Such a support includes activated alumina having a fairly high surface area. The acidid functionality can be conferred by Bronsted and/or Lewis acids. For example, the acidity may be conferred by Lewis and Bronsted acid sites on a support such as $\gamma$-alumina. Or activated aluminas. The catalyst may contain a promoter quantity of an alkali metal halide, such as a cesium halide. Other promoters may also be used. Typically the catalyst is a $\gamma$-alumina, or a silica alumina, having a surf ace area of at least about 50 $m^2/g$ (more preferably from 100–250 $m^2/g$) and which also has the moderate or high acidity attendant with such alumina containing compositions of this type.

The process of this invention is conducted using defined oxidation conditions. It may be conducted as a continuous, semicontinuous or batch method.

The product of this invention comprises an aldehyde. The aldehyde products of the invention have the many utilities known for them. As indicated above, they may be used as chemical intermediates.

DESCRIPTION OF PREFERRED EMBODIMENTS

This invention relates to the partial oxidation of non allylic, terminal, or vinylidene olefins with molecular oxygen. In a preferred embodiment, the process comprises contacting oxygen and such an olefin in the presence of a catalyst containing silver metal on an activated alumina support. The olefin used in this invention does not contain any allylic hydrogens, i.e., any hydrogen on a fully saturated carbon atom which is adjacent to a carbon to carbon double bond.

For the purpose of this invention, the term "partial oxidation" means oxidation to an organic product. The term is used to contrast with a complete oxidation of an olefin; in such a process the products would be carbon dioxide and water.

This invention is broadly applicable to olefins which:

1. have at least one carbon, in an aliphatic carbon-to-carbon double bond, bonded to two hydrogen atoms, 2. do not have any allylic hydrogens, or any hydrogen atoms bonded to a carbon atom that is directly bonded to an aromatic ring, and 3. do not have any other substituents which substantially interfere with the process. Olefins which satisfy these three criteria can be designated as "suitable olefins". This term means that the olefins are suitable, i.e. applicable for use in the process of this invention.

With regard to characteristic (3) above, applicable olefins have substituents selected from hydrogen and organic radicals which are:

(i) stable or substantially stable under the reaction conditions employed., that is, they do not decompose to a non tolerable extent during the course of the reaction, (ii) inert or substantially inert under the reaction conditions employed; that is they do not enter into any extraneous side reactions during the process to a non-tolerable extent, and (iii) acceptable for use in the process; that is, they do not interfere with the process by steric hindrance, or by changing the electronic character of the atoms or groups involved in the process, in a manner which unduly retards the process, or by poisoning the catalyst, or in any other manner interfere with the process of the invention to a non tolerable extent.

Substituents that meet criteria (i)–(iii) set forth above, can be referred to as "suitable substituents". This term signifies that such substituents are applicable for use in this invention since they do not substantially interfere with the process; in other words, that they may appear in an olefin which can be converted into an aldehyde according to the process of the invention. A skilled practitioner will recognize that there are two factors for consideration in connection with the above criteria. First is the chemical composition of the substituent itself. Some substituents are largely inert under the reaction conditions employed, others are more labile. The second factor is the position of the substituent in the molecule. A substituent may not be appropriate in one position but may be appropriate in another. A case in point are basic groups which have such a degree of basic character that they may tend to poison the catalyst. If such groups are positioned in the molecule so that they may be neutralized by an acidic group in the molecule, or in another molecule, they may be suitable for use in this invention.

It is within the skill of the art to determine by simple experimentation whether an olefin is suitable for use in this invention. A practitioner uses the olefin and follows the teachings of this specification applying the skill of the art. If no aldehyde product is obtained, the olefin is not suitable. Detection of aldehyde product indicates that the olefin is suitable for use in this invention.

Examples of suitable substituents are halo, amide, keto, ether and carboxyester groups. Of the halide radicals, the bromo, chloro and fluoro radicals are preferred because they are generally more readily available. However, iodo compounds can be used. The amide radicals may be unsubstituted,

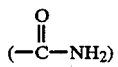

substituted

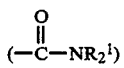

wherein one or both of the $R^1$ radicals is an organic group.

The ether, keto, and carboxyester groups also contain organic groups which are represented by $R^1$ in the above formulas. Preferably $R^1$ is a hydrocarbyl radical, i.e. a radical solely composed of carbon and hydrogen. However, $R^1$ may be substituted with a non hydrocarbyl, suitable group, such as those discussed above. (The radical $R^1$ is further defined below.)

Of the olefins having the above criteria, certain are preferred. First, because they are generally more available, it is preferred to use olefins having from two to about 20 carbon atoms. In this regard however, it is to be understood that olefins having more carbon atoms can be used. A preferred class of olefins is solely composed of carbon and hydrogen. Another class of preferred olefins has non hydrocarbyl substituents such as those referred to above, or a heterocyclc radical such as illustrated below.

Of the olefins discussed above, it is preferred that they have the formula:

wherein each R is hydrogen or an organic group. As can be seen from formula (I), both terminal and vinylidene olefins are applicable in the process. Preferably R is hydrogen or:

(a) $+CH=CH)_nCH=CH_2$ wherein n is equal to 0,1, or 2, or (b) $+CH=CH)_n-OR^1$ wherein n has the same significance as above, $R^1$ is alkyl, aryl, substituted alkyl, or substituted aryl, or (c) -tertiary alkyl or substituted tertiary alkyl, or (d)

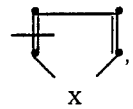

wherein X is S, O, or $NR^1$, and $R^1$ is defined above.

Of the olefins described above, a particularly preferred class of olefins for use in this invention has the formula:

$$CH_2=CH-R^2 \quad (II)$$

wherein $R^2$ is selected from $-CH=CH_2$, tertiary alkyl radicals, including the tert butyl radical and higher homologs thereof, aryl radicals, and carboxyester and halogen substituted aryl radicals. Highly preferred aryl radicals are phenyl, naphthyl, and hydrocarbyl substituted phenyl and naphthyl radicals.

Highly preferred, exemplary olefins which satisfy the above criteria are 1,3-butadiene, styrene, and 3,3-dimethyl-1-butene, and the like. The most preferred reactant for this invention is 1,3-butadiene (which is also referred to herein as "butadiene" or $C_4H_6$.) For the purpose of this invention, 1,3-butadiene and similar materials are considered free of allylic hydrogens because the carbon atoms alpha to a double bond are not saturated.

The catalyst employed is heterogeneous, i.e., not soluble in the reaction mixture. The catalyst can be used in a reaction with gaseous or liquid reaction systems. When desired, the reaction mixture can contain an inert liquid reaction medium to facilitate contacting the reactants, e.g., when the olefin is a solid at reaction temperature. The reaction medium may be selected from liquid hydrocarbons or ethers, such as tetrahydrofuran or hexanes.

The silver catalyst required for the practice of the present invention can be employed in either supported or unsupported forms. Preferably it is employed with a support such as an acidic alumina. When not loaded on a support, the silver is used in a system which supplies an acidic function. Thus, the system can comprise an acid, or a substance which yields an acid under the process conditions employed.

When a support is employed, the loading level of silver on support typically falls within the range of about 0.5 up to 50 weight percent, calculated as elemental silver and based on the total weight of finished catalyst. Preferably, the loading level of silver on support falls within the range of about 1 up to 30 weight percent elemental silver; with loading levels in the range of about 1 up to 20 weight percent being most preferred.

It is presently preferred to apply the silver to a solid support for efficient use of the expensive silver component. Typical catalyst supports include alumina, e.g., $\gamma$-alumina or activated aluminas, silica alumina, silica, and the like, as well as mixtures of the above.

Typically, these solid supports will have a surface area of at least about 50 $m^2/g$. Preferred supports will have a surface area of more than about 100 $m^2/g$ and will be at least moderately acidic in character. The presently most preferred supports have surface areas of from about 150 m²/g, to about 250 m²/g and include acidic and activated alumina, e.g., γ-alumina, and silica alumina mixtures. Supports of this type generally have the necessary acidity for use in this process. It is not necessary to measure the acidity of a catalyst support to determine if it is useful in this invention. Gamma aluminas and activated aluminas having a surface area of at least about 50m²/g, and similar supports, e.g., silica and silica aluminas, have the requisite acidity.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas liquid solid contacting, catalyst durability, and the like make the use of defined shapes such as spheres, pellets, extrudates, rings, saddles, and the like preferred.

Especially preferred catalysts are those which have been treated within the range of 10 up to 10,000 ppm, more preferably 200 to 2000 ppm, based on the total weight of catalyst, including support, of at least one promoter selected from:
(1) the salts of alkali metals,
(2) the salts of alkaline earth metals,
(3) hydrogen halides,
(4) acid halides,
(5) elemental halogens, and
(6) organic halides, Exemplary salts of alkali metals include sodium nitrate, sodium sulfate, sodium chloride, sodium bromide, rubidium nitrate, lithium sulfate, lithium chloride, cesium nitrate, and the like: exemplary salts of alkaline earth metals include barium nitrate, calcium nitrate, calcium chloride, and the like;

Exemplary hydrogen halides include HCl, HBr, and the like; exemplary acid halides include HOCl, HOBr and the like; and the elemental halogens include chlorine, bromine and iodine. The halogens may be dissolved in appropriate concentrations in a suitable solvent such as an organic halide of the type described below.

Exemplary organic halides include carbon tetrachloride, carbon tetrabromide, trichloroethylene, chloroform, bromoform, methylene chloride, methylene bromide, ethylene dibromide, ethylene dichloride, vinyl chloride, chlorobenzene, bromobenzene, α-chlorotoluene, 2-chlorotoluene, and the like. The organic halides can be used to prepare a promoted catalyst, and they also can be added to the olefin containing feed stream prior to reaction; alternatively, they can be added (in the appropriate quantities) at the reaction zone during reaction. Typically the organic halides are gaseous at ambient conditions or exist in the vapor phase under reaction conditions. Useful levels of organic halides in the feed stream are generally between 2-1000 ppm by volume. The appropriate level of organic halide in the feed stream or added to the reaction zone is determined by catalyst performance.

Those of skill in the art recognize that the above recited compounds are merely illustrative of the compounds which are useful as promoters in the practice of the present invention, and that many other compounds which fall within the generic categories set forth above can also be identified, and would be expected to also impart enhanced activity and/or selectivity to the catalyst employed in the practice of the present invention.

Of the above compounds, the organic halides and alkali metal halides are most preferred. Exemplary preferred alkali metal halides include cesium chloride, rubidium chloride, potassium chloride, sodium chloride, sodium bromide, potassium bromide, rubidium bromide, cesium bromide, and the like.

Those of skill in the art will also recognize that catalysts employed in the practice of the present invention can include additional components which may modify catalyst activity and/or selectivity. Such additives may be incorporated into the finished catalyst because their presence aids catalyst preparation, e.g., binders, die lubricants, and the like; or additives may be incorporated as extenders to reduce the cost of catalyst preparation; or additives may be incorporated to extend the operating ranges for reaction temperature and/or pressure; or additives may be incorporated to increase catalyst lifetime under reaction conditions and/or to modify the amounts of catalyst promoters employed to produce enhanced catalyst activity. It is recognized, of course, that some additives (e.g., cesium) are suitably employed in very low levels (i.e., milligrams of additive per gram of catalyst); while other additives (i.e., binders, diluents, and the like) are suitably employed at significantly higher levels (i.e., as a significant percentage of the total catalyst weight).

Supported catalysts can be prepared employing techniques well known to those of skill in the art, such as, for example, by precipitation of the active metals on the support, by impregnation, by coprecipitation of support and active metals, by grinding together solid support and active metal(s) in particulate form; and the like. When a promoter is also present in the catalyst, the order in which it is incorporated into the catalyst is not critical, i.e., the support can be contacted with a silver source, then promoter; or the support can be contacted with promoter, then a silver source; or the support can be contacted simultaneously with both promoter and a silver source; and other such variations.

Most any source of silver is suitable for use in preparing the catalyst employed in the practice of the present invention. Since a preferred method for preparation of supported catalyst involves impregnation of support with a solution of a silver compound, soluble silver compounds are a presently preferred source of silver. Exemplary compounds are silver nitrate, silver oxalate, silver acetate, and the like. Those of skill in the art recognize that certain organic silver compounds require the addition of ammonia or an amine in order to solubilize the organic silver compound in aqueous medium; thus, the use of such solvation promoting additives is contemplated in the practice of the present invention.

The process of the present invention is carried out under oxidation conditions, i.e., in the presence of sufficient quantities of an oxygen-containing gas to provide a molar ratio of olefin to oxygen in the range of about 0.01 up to 20. While greater or lesser quantities of molecular oxygen can be employed, sufficient quantities of oxygen should be provided to insure that undesirably low levels of olefin conversion do not occur, while excessively high oxygen concentrations should be avoided to prevent the formation of explosive mixtures.

Suitable oxygen-containing gases include air, oxygen enriched air, substantially purified oxygen, oxygen diluted with inert gases such as $N_2$, Ar, $CO_2$ or $CH_4$, and the like.

Suitable reaction temperatures fall within the range of about 150° C. up to 325° C. At lower temperatures, the reaction may proceed so slowly as to be impractical, while at higher temperatures undesirable levels of by products, e.g., carbon dioxide, may be obtained, preferred reaction temperatures fall within the range of about 175° C. up to 300° C.; with temperatures in the range of about 200° C. up to 275° C. being most preferred.

The reaction pressure can vary within wide ranges, with typical limits of about 0.1 up to 100 atmospheres being chosen primarily as a function of safety, handling equipment and other practical considerations, preferably, reaction pressure is maintained in the range of about 1 up to 30 atmospheres.

Reaction times suitable for the practice of the present invention can vary within wide ranges. Generally, the olefin, oxygen and catalyst are maintained in contact for a time sufficient to obtain olefin conversions in the range of about 0.5 up to 75 mole percent. Reaction times sufficient to obtain olefin conversion in the range of about 5 up to 30 mole percent are preferred for efficient utilization of the reactor capacity.

Those of skill in the art recognize that the actual contact times required to accomplish the desired conversion levels can vary within wide ranges, depending on such factors as vessel size, olefin to oxygen ratios, the silver loading level on the catalyst, the presence or absence of any catalyst modifiers (and their loading levels), the reaction temperature and pressure, and the like.

The invention process can be carried out in either batch or continuous mode. Continuous reaction is presently preferred since high reactor throughput and higher purity product is obtained in this manner. The batch mode is satisfactorily employed when high volume of reactant throughput is not required, for example, for liquid phase reactions.

For continuous mode of reaction carried out in the gas phase, typical gas hourly space velocities (GHSV) fall within the range of about 100 up to 30,000 hr$^{-1}$ GHSV in the range of about 200 up to 20,000 hr$^{-1}$ are preferred, with GHSV in the range of about 300 up to 10,000 hr$^{-1}$ being most preferred because under such conditions the most desirable combination of feed olefin conversion and product selectivities are obtained.

When a continuous mode of reaction is carried out in the liquid phase, typical liquid hourly space velocities (LHSV) employed will give contact times analogous to that obtained at the GHSV values given above. Most preferably. LHSV employed will fall in a range so as to produce the most desirable combination of feed olefin conversion levels and high product selectivity.

Recovery of product produced in the practice of the present invention can readily be carried out employing techniques well known by those of skill in the art. For example, where reaction is carried out in the continuous mode, unreacted starting material is initially separated from reaction products; and the desired product then isolated from the resulting product mixture by distillation, crystallization, extraction, or the like.

The invention will now be described in greater detail by reference to the following non-limiting examples.

EXAMPLE 1—CATALYST PREPARATION

Catalysts were typically prepared by impregnation of a support with a solution of a silver compound (and optionally a promoter) in several volumes of solvent relative to the volume of support being treated. Thus, for example, a 1.5% Ag (as determined by neutron activation analysis) on $\gamma$-$Al_2O_3$ (Harshaw 3970p) support was prepared by dissolving 0.071 grams of Kodak silver nitrate in 50 mL of distilled water. To this solution, 3.0 grams of an alumina having a surface area of 190 $m^2/g$ was added. The mixture was slurried for 30 minutes at 50° C., before the water was removed by rotary evaporation at 60° C.

The resulting powder was then dried for 60 minutes at 120°–160° C. in a forced air oven. This material could be calcined and used directly for oxidation of non allylic olefin feed or treated with a promoter and then calcined, or preferably calcined and then treated with a promoter.

Calcinations were conducted in an oxygen-containing atmosphere (air or oxygen-supplemented helium) at about 350° C. for about 4 hours. Following calcination, all catalysts were subJected to an activation treatment at a temperature in the range of about 300°–350° C. in an atmosphere initially containing about 2–5% hydrogen in an inert carrier such as helium or nitrogen. The hydrogen content of the activating atmosphere was gradually increased up to a final hydrogen concentration of about 20–25% at a controlled rate so that the activation temperature did not exceed 350° C. After the temperature was maintained for about 1 hour at a hydrogen concentration in the range of about 20–25%, catalyst was ready for use.

When the Ag/$Al_2O_3$ catalyst was treated with a promoter, a quantity of catalyst was contacted with several volumes of aqueous promoter, then dried as previously described. Thus, for example, 0.968 g of freshly calcined catalyst composed of 5% Ag supported on Al-1605P $Al_2O_3$ powder was added to 9.68 ml of an aqueous solution containing 0.10 mg CsCl/ml solution. This resulting slurry was agitated for 30 minutes at 50° C. before the $H_2O$ was removed by rotary evaporation at 60° C.

Typical catalysts prepared in this manner are listed in the following table:

TABLE 1

| Catalyst | Silver loading (weight %) | Support | Manufacturer's* Catalyst No. |
|---|---|---|---|
| 1 | 5 | $\alpha$-$Al_2O_3$ | Al-3980T |
| 2 | 1.5 | $\gamma$-$Al_2O_3$ | Al-3970P |
| 3 | 5 | $\gamma$-$Al_2O_3$ | Al-1605P |
| 4 | 5 | $\gamma$-$Al_2O_3$ | Al-1609P |
| 5 | 3 | $\gamma$-$Al_2O_3$ | Al-3916P |

*Al-3980T, alumina catalyst, Harshaw Chemical Company, 23800 Mercantile Road, Beachwood, Ohio, 44122. Surface area, 3.3 $m^2$g; apparent bulk density, 75 lbs./cu. ft.; pore volume, 0.27 cc/g.
Al-3970P, alumina catalyst, Harshaw Chemical Company. Surface area, 190 $m^2/g$; apparent bulk density, 50 lbs./cu. ft.; particle size distribution: <30 microns, 15%.
Al-1605P, alumina catalyst, Harshaw Chemical Company. Surface area, 222 $m^2/g$; apparent bulk density, 63 lbs./cu. ft.; pore volume, 0.59 cc/g.
Al-1609P, alumina catalyst, Harshaw Chemical Company. Surface area, 275 $m^2/g$; apparent bulk density, 53 lbs./cu. ft.; particle size distribution: <80 microns, 85%; <45 microns, 45%; <30 microns, 20%.
Al-3916P, alumina catalyst, Harshaw Chemical Company. Surface area, 185 $m^2/g$; apparent bulk density, 49/lbs./cu. ft.; pore volume, 0.43 cc/g; particle size distribution: <80 microns, 90%; <45 microns, 55%; <30 microns, 25%.

As noted, catalyst supports for this invention can comprise materials that are commercially available.

It is to be understood that both the impregnation and promoter steps can be carried out using substantially less than several volumes of solution per unit amount of catalyst. It is also to be understood that catalysts useful in this invention can be prepared without a discrete calcination step as described above.

EXAMPLE 2—PROCESS RESULTS-EFFECT OF CATALYST SUPPORT

In all of the following catalyst evaluation runs, catalysts were evaluated under steady state conditions in a one atmosphere flow reactor system.

The reactor tube was constructed of Pyrex® glass and the catalyst charge (between 0.1 and 20.0 g) was held in place by means of a Pyrex frit. The geometries of the reactor and catalyst particles as well as bed depth were chosen to maintain and measure the true kinetic and catalytic aspects of the reaction. A chromel/alumel thermocouple sheathed in stainless steel was embedded within the catalyst bed to measure the true reaction temperature.

The feed gases, i.e., 1,3-butadiene, and $O_2$, as well as the diluent He, were added using mass flow controllers, which permitted highly accurate and reproducible flow rates of $C_4H_6$, $O_2$, and He regardless of pressure changes from the supply cylinders or the reactor system downstream from the controllers.

Reaction product analyses (as well as feed composition analyses) were made using an in-line gas sampling loop connected directly to the inlet of a Varian 3760 gas chromatograph. Both thermal conductivity (TC) and flame ionization (FI) detectors [connected in series below the packed Chromosorb 101 column (8 ft. by 2mm i.d. pyrex capillary column)] were used to analyze all of the reaction products. The TC detector gave quantitative analyses for $O_2$, $CO_2$, $H_2O$, and HCHO (if present), while the FI detector was used for organic molecules such as $C_4H_6$, butadiene monoxide, crotonaldehyde, 2,5-dihydrofuran, furan and acrolein. Further, by means of a switching valve, it was possible to divert the feed stream through the in-line sample loop prior to passage over the catalyst. In this way, quantitative analysis of the feed stream and comparison to the corresponding data from the reactor effluent were possible, thereby providing very accurate measurements of both conversion levels and product selectivities. Output from both the TC and FI detectors were integrated using computing integrators which were programmed to give both absolute quantities and rates of formation. All reactor exit lines were heated and maintained at 125°–140° C. to prevent product condensation.

The GC analysis was performed using the following temperature programming schedule: an initial temperature of 100° C. was held for 5 minutes, followed by a temperature program rate of +10° C./min up to a final temperature of 200° C. which was then held for 7 minutes. The helium GC carrier rate was 20 mL/min.

Reaction parameters and results are presented in Table 2 below.

The following data in Table 2 were obtained at a reaction temperature of 225° C. and a pressure of 1 atmosphere. The feed compositions are expressed as volumetric ratios and are as posted for each catalyst. The overall flow rates are expressed as GHSV in $hr^{-1}$.

TABLE 2

| Catalyst No. | 1 | 2 | 3 | 4 | 5 |
|---|---|---|---|---|---|
| Surface Area of Supprt | 3.3 | 190 | 220 | 275 | 185 |
| Approximate Level of Acidity | low | moderate | higher | higher | moderate |
| Feed Composition (He/$C_4H_6$/$O_2$) | 0/1/1 | 0/1/1 | 2/1/1 | 0/1/1 | 4/1/1 |
| GHSV ($hr^{-1}$) | 1200 | 2400 | 4400 | 1900 | 1600 |
| Products* | | | | | |
| $CO_2$ | 6 | 19 | 14 | 20 | 29 |
| Furan | 12 | 5 | 5 | 5 | 3 |
| Acrolein | 24 | 14 | 21 | 22 | 14 |
| Butadiene Monoxide | 47 | 2 | 7 | 4 | 1 |
| Crotonaldehyde | 11 | 60 | 53 | 49 | 53 |
| % $C_4H_6$ Conversion | 0.03 | 0.03 | 0.04 | 0.4 | 0.08 |

*Products expressed as % selectivity based on moles of $C_4H_6$ converted.

The process of Run 1 in Table 2 does not comprise a method of this invention, and is included in the above table for comparative purposes. As can be seen, the catalyst employed in that run has a very low surface area and also has a low acidity. Use of such a catalyst results in a poor rate of conversion to crotonaldehyde, and a poor selectivity to that product. Catalysts useful in this invention provide a comparatively high conversion to aldehyde products compared to other materials such as epoxides.

The above data illustrate that catalysts comprising silver on high surface area, activated alumina, (i.e., alumina having a surface area of at least about 100 $m^2/g$ and attendant moderate or higher acid properties) readily and selectively produce crotonaldehyde from 1,3 butadiene.

EXAMPLE 3—EFFECT OF PROMOTERS

The effect of a catalyst promoter is illustrated by data in Table 3. Data set forth in that table was obtained using the same reaction parameters as for Table 2.

TABLE 3

| Catalyst | Catalyst No. 3 promoted with 1 mg CsCl per gram of finished catalyst | Catalyst No. 5 with feed containing 25 ppm of 1,2-dichloroethane |
|---|---|---|
| Feed Composition (He/$C_4H_6$/$O_2$) | 0/1/1 | 2/1/1 |
| GHSV ($hr^{-1}$) | 1020 | 1600 |
| Products* | | |
| $CO_2$ | 12 | 22 |
| Furan | 5 | 3 |
| Acrolein | 18 | 14 |
| Butadiene monoxide | 10 | 0 |
| Crotonaldehyde | 55 | 61 |

*Products expressed as % selectivity based on moles of $C_4H_6$ converted.

As demonstrated by comparison of the date in Table 3 with that of Table 2, the presence of a promoter can reduce the amount of oxidation of a olefin to $CO_2$ (i.e., complete oxidation); compare Catalyst 3 in Table 2 with promoted Catalyst 3 in Table 3. As shown by the comparison of those two runs, the selectively to acrolein is also reduced when the promoter is present. As suggested by the data, the selectively to desired crotonaldehyde in Run 3 of Table 2 could be enhanced using a process modification which decreases the amounts of non-selective reaction products, such as $CO_2$ and acrolein. Comparison of the data for Catalyst 5 in Table 2 with that for Catalyst 5 in Table 3 also demonstrates a further preferred embodiment of the invention. That embodiment comprises addition of an organic halide promoter to the olefin feed stream employed in the process.

Organic halides contemplated for this purpose include compounds of the structure $R^3X$, wherein $R^3$ is a hydrocarbyl radical or halogenated hydrocarbyl radical having in the range of 1 up to 8 carbon atoms, and X is any one of the halogens, preferably chlorine or bromine, and wherein $R^3$ contains at least one hydrogen atom which is sufficiently acidic so as to render $R^3X$ capable of undergoing dehydrohalogenation under the reaction conditions. Exemplary organic halides include $C_1$ compounds such as methyl chloride, methyl bromide, methylene chloride, methylene bromide, chloroform and bromoform, and the like; $C_2$ compounds such as ethyl chloride, ethyl bromide, dichloroethane, dibromoethane, vinyl chloride, dichloroethylene, trichloroethylene, and the like; $C_3$ compounds such as dichloropropane, dibromopropane, dichloropropene, dibromopropene, and the like; $C_4$ compounds such as chlorobutane, bromobutane, dichlorobutane, dibromobutane, chlorobutene, bromobutene, dichlorobutene, dibromobutene, and the like; $C_5$ compounds such as mono-, di-, tri-, tetra and pentachloropentanes or pentenes, mono-, di-, tri-, tetra- and pentabromopentanes or pentenes, cyclopentylchloride, cyclopentylbromide, and the like; $C_6$ compounds such as mono-, di-, tri-, tetra-, penta and hexachlorohexanes or hexenes, mono-, di-, tri-, tetra-, penta- and hexabromohexanes or hexenes, cyclohexylchloride, cyclohexylbromide, chlorobenzene, bromobenzene, and the like; $C_7$ compounds such as chlorotoluene, bromotoluene, benzyl chloride, benzyl bromide, mono-, di-, tri-, tetra-, penta-, hexa- and heptachloroheptanes or heptenes, mono-, di-, tri-, tetra-, penta-, hexa-, and heptabromoheptanes or heptenes, chlorocycloheptane, bromocycloheptane, and the like; $C_8$ compounds such as mono-, di-, tri-, tetra-, penta-, hexa-, hepta-and octachlorooctanes or octenes, mono-, di-, tri-, tetra-, penta-, hexa-, hepta-, and octabromooctanes or octenes, and the like; as well as mixtures of any two or more thereof.

The halide preferably has 1 to about 8 carbon atoms. More preferably, the halide is a chloride or bromide. Still more preferably, it is a dichloride or dibromide such as 1,2-dichloroethane or 1,2-dibromoethane. Preferably the organic halide is added in an amount of from about 2 to 150 ppm to the olefin feed stream employed in the process.

As indicated above, the organic halide can be added to the oxidation reaction zone in a variety of ways. For example, it can be mixed with the olefin to be oxidized and/or the oxygen containing gas prior to contacting with the catalyst, or the organic halide can be introduced to the reaction zone separately from the feed olefin and/or the oxygen containing gas.

As shown by Table 3, with 1,2-dichloroethane the formation of $CO_2$ is considerably lowered, giving an increased selectivity to crotonaldehyde. The data in Table 2 and Table 3 also clearly indicate that a promoter is not necessary for the process of this invention.

The process of the above examples can be extended to use of the other reactants, catalyst and promoters set forth above, using reaction conditions taught by the above detailed description.

A skilled practitioner can make substitutions and modifications of the process described above without departing from the scope and spirit of the appended claims.

We claim:

1. Process for the preparation of crotonaldehyde, said process comprising reacting 1,3-butadiene with oxygen in the presence of a catalytic quantity of a catalyst consisting essentially of metallic silver on a support, said support selected from the class consisting of alumina, silica-alumina, and silica, said support having a surface area of at least about 50 $m^2/g$; said process being conducted at a temperature of from about 150° C. to about 325° C., and at a pressure of from about 0.1 to about 100 atmospheres.

2. The process in accordance with claim 1 wherein said oxygen containing gas is selected from the group consisting of:
   air,
   inert gas diluted air,
   inert gas diluted oxygen,
   oxygen enriched air, and
   substantially purified oxygen.

3. process of claim 1 wherein said supported silver catalyst has from about 0.5 to about 50 weight percent metallic silver.

4. The process in accordance with claim 3 wherein said silver catalyst further consists of from 10 up to 10,000 ppm, based on the total weight of catalyst, including support, of at least one promoter selected from the group consisting of:
   (a) nitrate, chloride and bromide salts of alkali metals and alkaline earth metals,
   (b) organic chlorides and bromides of 1-8 carbon atoms,
   (c) HCl and HBr
   (d) HOCl and HOBr, and elemental chlorine, bromine, and iodine,
as well as mixtures o: any two or more thereof.

5. The process in accordance with claim 4 wherein said promoter is a halide or a nitrate of an alkali metal.

6. The process of claim 4 wherein said promoter is an organic halide having the formula $R^3X$ wherein X is a halogen and $R^3$ is a hydrocarbyl radical or a halogenated hydrocarbyl radical having from 1 to about 8 carbon atoms which has at least one hydrogen atom that is sufficiently acidic to render $R^3X$ capable of forming HX in said process.

7. The process of claim 6 wherein said organic halide is dichloroethane.

8. The process in accordance with claim 1 wherein said silver catalyst consists essentially of:
   from about I up to 30 weight percent silver,
   from about 10 up to 10,000 ppm of an alkali metal chloride, bromide, or nitrate, or mixture of said halide and nitrate, and
   an alumina support having a surface area of at least about 100 $m^2/g$;
   said weight percentages being based on the total weight of catalyst.

9. The process in accordance with claim 8 wherein said alkali metal halide is selected from the group consisting of cesium chloride and cesium 10. The process in accordance with claim 8 wherein said contacting is carried out at a temperature in the range of about 175° up to 300° C., at a pressure in the range of about 1 up to 30 atmospheres for a time sufficient to obtain olefin 1,3-butadiene conversion in the range of about 5 up to 30%.

11. The process in accordance with claim 1 wherein said silver catalyst consists essentially of:
   from about 1 up to 20 weight percent silver,
   from about 200 up to 2,000 ppm of an alkali metal chloride or bromide, and
   an alumina support having a surface area of at least about 100 $m^2/g$;
   said weight percentages being based on the total weight of catalyst.

* * * * *